United States Patent [19]

Katz

[11] 4,128,877

[45] Dec. 5, 1978

[54] METHOD OF OBTAINING A UNIQUELY DETERMINED CROSS-SECTIONAL RECONSTRUCTION FROM X-RAY PROJECTIONS

[76] Inventor: Myron B. Katz, 1633 First St., Apt. A, New Orleans, La. 70130

[21] Appl. No.: 783,083

[22] Filed: Mar. 31, 1977

[51] Int. Cl.$^2$ .................... G01N 23/08; G06F 15/42
[52] U.S. Cl. ................... 364/414; 250/416 R; 250/445 R
[58] Field of Search .................. 364/414, 300; 250/445 T, 445 R, 363 R, 363 S, 416 R, 416 TV

[56] References Cited

U.S. PATENT DOCUMENTS

| | | | |
|---|---|---|---|
| 3,983,399 | 9/1976 | Cox, Jr. et al. | 364/414 |
| 4,044,240 | 8/1977 | Cox, Jr. et al. | 364/414 |
| 4,063,097 | 12/1977 | Barrett et al. | 250/445 T |

OTHER PUBLICATIONS

Cho, Z. H.; General Views on 3-D Image Reconstruction and Computerized Transverse Axial Tomography; IEEE Trans. on Nuclear Science, vol. NS-21, Jun. 1974, pp. 44–70.
Chang et al.; Analog Reconstruction from X-Ray Projections; IBM Tech. Disc. Bulletin, vol. 15, No. 12, May 1973, pp. 3712–3714.

Primary Examiner—Charles E. Atkinson
Assistant Examiner—Errol A. Krass
Attorney, Agent, or Firm—Townsend and Townsend

[57] ABSTRACT

A method of obtaining a uniquely determined reconstruction of a cross-section of an object from a number of projected images of the object. X-rays are directed to pass through the object in parallel rays to project an image of the object onto a detector. Each projection is made at an angle selected in accordance with certain critical parameters and measured from a predetermined reference. The critical parameters include the resolution of the reconstruction to be made and the required resolution in the projection data for each projection. The projection data so obtained is then mathematically combined to produce a grid-like reconstruction on a display unit. If desired, the method includes a technique for improving resolution in the reconstruction by obtaining additional and overlapping projection data, yet maintaining the uniqueness of the reconstruction.

4 Claims, 9 Drawing Figures

METHOD OF OBTAINING A UNIQUELY DETERMINED CROSS-SECTIONAL RECONSTRUCTION FROM X-RAY PROJECTIONS

BACKGROUND OF THE INVENTION

1. Field of the Invention

The invention relates to a method for reconstructing a cross-section of an object from a number of X-ray projected images of the object and, more particularly, to a method of obtaining a cross-sectional reconstruction of the object that is uniquely determined.

2. Description of the Prior Art

The theory of reconstructing a three-dimensional or a two-dimensional cross-sectional view of an object from projections of the object has been known since at least 1917 when the Austrian mathematician J. Radon proved that objects can be reconstructed uniquely from the infinite set of all projections. However, full exploitation of such reconstruction techniques have had to await the arrival of modern computers and other developments in the art. Thus, it has been only recently that reconstruction techniques have been used to open a new era in the practice of medicine, allowing non-invasive procedures to be used to determine the internal structures of the human body.

Techniques for projecting the image of the internal structures (i.e., bones, organs, etc.) of the body are known. Many such techniques direct a diverging plurality of X-rays through the body to project an image of the internal structure onto a receiving element such as an X-ray plate. Invaluable as this technique is, it has long been difficult or impossible to distinguish one internal organ from another in view of their overlap on the film. This is particularly true when the X-ray density of one structure differs only slightly from the density of a neighboring one, as is often the case with a tumor and the tissue in which it is embedded.

One attempt to minimize this problem involves obtaining a number of X-ray projections from different angles to expose the internal organs in different relative positions. The pictures of the projected images are then viewed by an experienced physician who makes a qualitative determination of the internal structure of the patient so viewed.

A recent advance in the art builds upon the above technique by combining X-ray pictures through a mathematical procedure which yields a representation of the internal structure. With such vital information available, diagnosis can become more accurate, and more precise guidance can be given to the hand of the surgeon and to therapeutic radiation aimed at a tumor.

Thus, devices are on the market today which process X-ray projection data and produce a reconstruction (i.e., a finite dimensional approximation) of the actual mass distribution of a cross-section of the patient's body. These devices operate by directing X-rays through the patient's body in parallel rays as the patient (or the apparatus) is rotated in steps around a single axis. A photographic image is made at each step; that is, for each projection, structures in the patient's body lying in a plane perpendicular to the axis of rotation would be recorded on a single one-dimensional line. By measuring the X-ray density along that line on each image, the information from the desired plane is isolated. From this information a single two-dimensional plane is reconstructed and, if desired, the sequence of such planes are merely stacked to get a full three-dimensional picture.

Such devices utilize a collimator that is placed in front of an X-ray source to produce the parallel X-rays. An X-ray detector is positioned on the opposite side of the patient from the source and the collimator. The source, the collimator and the detector then scan across the patient in a direction perpendicular to the beam of the X-rays.

The Central Research Laboratories of EMI Limited of England have developed such a device for obtaining cross-sectional reconstructions of a patient's head. Known as the EMI Scanner, this instrument is designed primarily for scanning the brain. The system takes a projection at each of 180 different angles in one degree increments. Each projection is actually 160 different measurements so that 160 times 180 observations are entered into a computer for processing.

The next step in the method used by the EMI Scanner is the use of a computer-implemented algorithm which transforms the projection data into the desired reconstruction. For some time, the algorithm called the Algebraic Reconstruction Technique developed by Herman, Gordon, and Bender ("Algebraic Reconstruction Techniques [ART] for three-dimensional electron microscopy and X-ray photography", J. Theor. BIOL XXIX [1970], 471–481), was used to perform the desired transformation. Later the Convolution method, developed by Ramachandran and Lakshminarayanan ("Three-dimensional reconstruction from radiographs and electron micrographs: application of convolutions instead of Fourier transforms." Proc. Nat'l. Acad. Sci. USA LXVIII (1971), 2236–2240.), was implemented. Finally, the reconstruction is displayed on a cathode ray tube or T.V. screen.

However, despite the efforts of many who work in this art, the issue of uniqueness of reconstructions obtained by known prior art methods has remained an open and illusive question. As used herein, a uniquely determined reconstruction means that there is only one reconstruction which is in closest agreement with the projection data — regardless of how "closeness" is defined.

It has long been known that any method of reconstruction is applied to a finite amount of real data (in contrast to the infinite number of mathematically precise projections required by Radon's theorem), and yields reconstructions that are at best only estimates of the object's actual structure. Moreover, the relative accuracy of various mathematical models has been found to depend on the nature of the data collected. Therefore, since it must be accepted that only a finite number of projections is practically available, the theoretical results which require more projection data are not applicable.

Additionally, experience has indicated, and supported by current mathematical analysis, that theretofore no test devised could predict the reliability of any particular reconstruction. More emphatically, this is not simply a question of being slightly off somewhere within the reconstruction, but important features, such as the existence and position of brain tumors, were inexplicably missing. In fact, 20 percent of the reconstructions produced by known devices have been considered incorrect. In short, present methods of obtaining reconstructions from projections lack the quality of being uniquely determined.

Heretofore, such inaccuracies and errors have been thought to be a consequence of the choice of the reconstruction algorithms, data collection, and/or the display of the information. Very little, if any, thought has been given, so far as is known, to the choice of angles from which the projections are taken and the relationship between the angles of each projection, the resolution in the projection data, and the resolution in the reconstruction as they affect the uniqueness of that reconstruction.

SUMMARY OF THE INVENTION

A method of obtaining a uniquely determined reconstruction of a cross-section of an object from a number of projected X-ray images of the object is disclosed. X-rays are directed to pass through the object in parallel rays, projecting an image of the object onto a detector. Each projection is made at a specifically determined angle selected in accordance with certain critical parameters, which include the resolution of the reconstruction and resolution in the projection data for each projection. The projection data so obtained is then mathematically combined to produce a grid-like reconstruction (composed of $n^2$ uniform squares) on a display unit. If desired, the method includes a technique for improving resolution in the reconstruction by, in effect, obtaining projection data in a series of overlapping projections and reconstructions.

Of the infinite number of angles that may be used for each projection, it has been found that there exists a finite set of particular angles, $\bar{\theta}(n)$, which have the practical advantage of requiring less restrictive resolution in the projection data. In addition, the utilization of angles selected from this set, $\bar{\theta}(n)$, will provide projection data that is more useful for creating a unique reconstruction. This set of particular angles, $\bar{\theta}(n)$, has elements of the form $\theta = \arctan p/q$ where p and q are relatively prime integers and $$0 \leq |p|, |q| \leq n.$$

The subset of angles $\{\theta_1, \theta_2, \ldots, \theta_m\}$ selected from the set $\bar{\theta}(n)$ are chosen in accordance with the resolution in the projection data. The required resolution in the projection data for the projection angle, $\theta = \arctan p/q$ is given by $$L/n \, (p^2 + q^2)^{-\frac{1}{2}}$$

where L is the length of a side of the reconstruction. In particular, use should be made of only those angles $\{\theta_1, \theta_2, \ldots, \theta_m\}$ selected from the set $\bar{\theta}(n)$, which provide a required resolution in the projection data (expressed by the above formula) that is at least as great or greater than the resolution of the projection data collecting device. Resolution is an empirically determined quantity that represents the minimum distance between two points of information for reliable discrimination of those points.

The reconstruction created by the method of the present invention are produced on a rastered picture composed of finitely many squares or "pixels" as they are known in the art. This reconstruction or, as used in the remainder of this description, reconstruction space is the same as that utilized by (black and white) television, newsprint, satellite telemetry, and the human eye for image production. In each case, a square is divided into $n^2$ smaller, uniform pixels of side L/n where L is the length of the side of the entire picture.

Further, the method of the present invention dictates that given a particular finite set of projections, there is a "maximal" number of pixels ($n^2$) in the checkerboard-like raster such that the reconstruction from the projection data is uniquely determined. That is, uniqueness of any reconstruction attempted according to this method will be maintained if $$n < 1 + \max\left(\sum_{j=1}^{m} |p_j|, \sum_{j=1}^{m} |q_j|\right),$$

where m is the number of angles selected from $\bar{\theta}(n)$ and each $p_j$ and $q_j$ are defined above.

Once the reconstruction space is specified (e.g., by defining the number, $n^2$, of pixels that make up the display) and the set of angles, $\{\theta_1, \theta_2, \ldots, \theta_m\}$, are determined from the criteria outlined above, the method proceeds as follows.

The method is used with a reconstruction system that comprises an X-ray source, a detector unit, a computer and a display unit. The X-ray source and detector unit are positioned in spaced relation, relative to one another, so that the object to be scanned may be positioned between the two.

X-rays are generated by the source and directed through the object, the body or head of a patient for example, so that the rays emerging are projected onto the detector unit and, in so doing, produce projection data. A projection with X-rays is taken at each one of the selected angles by rotating the source-detector unit through the angles about the body.

The projection data obtained by the detector unit are entered into the computer where the projections are mathematically combined to create a uniquely determined reconstruction of a cross-section of the object which the computer uses to generate a picture on the display unit, such as a cathode ray screen.

A number of advantages are obtained by the method of the present invention. An important advantage resides in the fact that the reconstruction obtained is uniquely determined. Thus, the problem heretofore encountered using reconstruction from projection techniques, such as unexplained absences of tumors, is obviated. The physician is provided with a non-invasive diagnostic technique upon which he can more fully rely.

The underlying work which gave rise to the method disclosed herein as well as the supporting mathematical derivations are contained in the Ph.D. Dissertation entitled "Questions of Uniqueness and Resolution in Reconstruction of 2-D and 3-D Objects from their Projections" by M. B. Katz, on file in the University of California Library and Xerox University Microfilms, Ann Arbor, Michigan and in a paper entitled "Improving the EMI Scanner" by the same author.

For a fuller understanding of the nature and advantage of the invention, reference should be had to the ensuing detailed description taken in conjunction with the accompanying drawings.

DESCRIPTION OF THE PREFERRED EMBODIMENT

When X-rays pass through matter, they are (approximately) absorbed in proportion to the density of that matter. Thus, if we record the intensity of X-rays that have passed through an object, we get a projection of the mass density. To determine a cross-section of the density distribution in an object, for example the head of a patient, then the physical problem is reduced to recovering that distribution from a finite number of radiographs.

Figure 1:
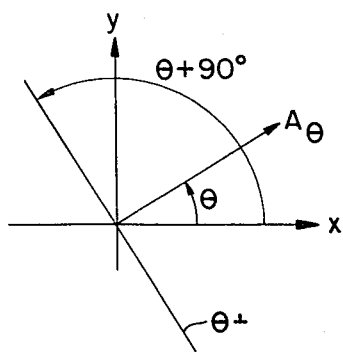
FIG. 1 is a graphical illustration of a projection onto a line in a direction measured $\theta°$ from a predetermined reference.

The mass distribution of the object can be described by its density at each point. Therefore, this discussion will use f, a real valued function defined on a plane, as representative of the coefficient of X-ray absorption at each point upon the particular cross-sectional plane. Because f represents a physical object, it is a non-negative function which is considered to be zero in air (since absorption of X-rays by air is small). Obtaining a radiograph is equivalent to projecting f in a predetermined direction through the object. Thus, as FIG. 1 indicates, a projection of f in the direction of $A_\theta$ onto the line $\theta^\perp$ is given by:

$$P_\theta f(v) = \int_{-\infty}^{\infty} f(v + tA_\theta)dt, \text{ for } v \text{ in } \theta^\perp \quad (1)$$

Thus, $P_\theta f$ is a function which is defined on the line $\theta^\perp$ and has the property that its value at any point, v, in $\theta^\perp$ depends only on that part of f defined on the line $v+tA_\theta$, where t is a real number.

When f represents the distribution of X-ray absorption in a cross-section of a human head, then $P_\theta f$ is usually just an X-ray or radiograph of that head read along the appropriate line on the photographic film.

Using this notation, the general mathematical question is to determine f from the observed data, i.e., ($P_{\theta_1}f$, $P_{\theta_2}f$, ..., $P_{\theta_m}f$). However, the practical problem is to determine a reconstruction, h, of f, where h is a member of a finite dimensional reconstruction space, Z(n). The reconstruction space used herein is the same one utilized by television or the human eye, namely a finite rectangular grid of small pixels (squares).

It has been discovered that obtaining a reconstruction, that is uniquely determined, from a projected radiograph requires that particular attention be given to the concept of resolution - in the projection data, $P_\theta f$, as well as in the reconstruction, h.

Resolution of an image or observation is generally defined as the size of the smallest part which can be reliably discriminated. For example, the medium upon which projections are recorded may be standard X-ray film composed of an emulsion of silver halide crystals. In general, exposure to radiation is recorded by a whole crystal — regardless of which portion of the crystal is irradiated. Thus, the minimum distance between two points of an image projected upon an emulsion of silver halide crystals must be greater than or equal to the diameter of the average exposed surface area of the crystals — normally referred to as the grain of the film. Therefore, limitations on the resolution in the projection data recorded by such a medium necessarily exist.

Resolution in the reconstruction is similarly defined. If the reconstruction space is defined as a square L × L grid divided into $n^2$ smaller uniform pixels, where on each of the smaller pixels the reconstruction assumes a constant value, then the resolution in the reconstruction would be defined as L/n.

The method of the present invention will show how to select the optimal picture resolution which can be obtained for a particular quality of projection data. In particular, if for a given resolution in the projection data, picture resolution attempted is too fine, then the uniqueness of a reconstruction is lost.

Figure 2:
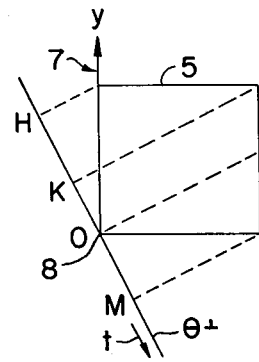
FIGS. 2 and 3 depict regions of projection data defined by the projected images of the vertices of a pixel into the line $\theta^\perp$ and illustrate how those regions vary as a function of the projection angle, $\theta$.
Figure 3:
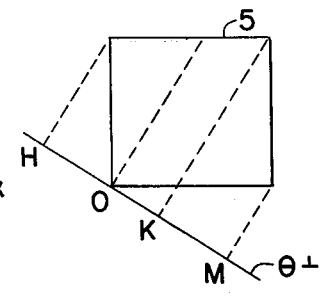

The problem of obtaining f from the projection data, $P_\theta f$, requires that as much of the information in $P_\theta f$ be available as possible. An explanation of the information in $P_\theta f$ requires an examination of the projection of the function which is contantly 1 on the (i, j)$^{th}$ pixel 5 (FIGS. 2 and 3) and zero everywhere else. Thus, referring to FIGS. 2 and 3, there is illustrated the projection of a single pixel 5 of Z(n) indicating how that projection depends upon $\theta$, the angle of projection. FIG. 2 shows $\theta$ between 0° and 45°, while FIG. 3 represents $\theta$ between 45° and 90°.

By considering the projection of the squares in this way (FIGS. 2 and 3) it can be seen that the region where the projection is non-zero has end points H and M. It is also clear that on the region with end points O and K, the projection of the square is constant. The integration along $\theta^\perp$ changes its local dependence at the points H, O, K and M for $\theta$ between 45° and 90° and L, K, O and M for $\theta$ between 0° and 45°.

The expression for the projection of the pixel 5 can be shown to demonstrate that there are only three regions along $\theta^\perp$ where the projection is non-zero and has distinct local dependence. Those regions have end points K, H, M and O in FIGS. 2 and 3; the set {K, H, M and O} is exactly the set of projected images of vertices of the pixel.

If the more general situation is considered, i.e., considering $P\theta f$ for arbitrary f in the reconstruction space Z(n) and an arbitrary $\theta$, we can let $v_1, v_2, \ldots, v_k, v_{k+1}$ be the projected images of vertices of pixels in the direction of $\theta$ onto the line $\theta^\perp$ (FIG. 1), then f in Z(n) has a projection, $P_\theta f$, which is completely determined by the k real numbers in the set:

{Average value of $P_\theta f$ on the interval ($v_i, v_{i+1}$): for i = 1, 2, ..., k}.

This fact tells us that if we desire all of the information in $P_\theta f$, then we need only determine the average value of $P_\theta f$ on certain regions, i.e., on those regions consisting of the subsets of $\theta^\perp$ with end points within the set of projected images of vertices of pixels in the direction of $\theta$ onto the line $\theta^\perp$. The significance of this fact derives from the concept of empirical resolution which will be discussed more fully below.

In practice, projection data only contains a finite amount of information. For this reason, experimenters have introduced the notion of resolution in any type of observational data. The projection data may be thought of as being as finite number of points on the recording medium (e.g., film, for example). As explained above, these points cannot be any closer than some minimal distance that depends on the nature of the way the observations are made. This distance, w, is defined herein as the available resolution of the projection data.

Thus, for empirical reasons, there is a number w which specified the smallest region in $\theta^\perp$ where $P_\theta f$ should be sampled. Certainly, w can vary from experiment to experiment, but there is always some limit on the fineness of the observations. It is necessary, therefore, that:

$$w \leq \min_i (|v_i - v_{i+1}|) \quad (2)$$

in order that all of the information in $P_\theta f$ be retrievable in practice, where $\{v_1, v_2, \ldots, v_{k+1}\}$ is the set of projected images of vertices of pixels.

It has been discovered that if the projection angle, $\theta$, is any angle satisfying $\tan \theta = p/q$ for p and q are relatively prime integers and letting n be any positive integer which exceeds both $|p|$ and $|q|$ so that Z(n) is specified, then the available resolution, w, in the projection, $P_\theta f$, so that all the information relevant to determining f can be utilized, must be no larger than L/n times the quantity $$(p^2 + q^2)^{-\frac{1}{2}} \quad (3)$$

L is the length of the side of the reconstruction.

It can be easily demonstrated from the immediately preceding concept that the minimum distance between the projected images of vertices of pixels in the direction of $\theta$ onto the line $\theta^\perp$ is relatively large within the set of angles defined by $\tan \theta = p/q$, where p, q are relatively prime integers and $0 \leq |p|, |q| \leq n$.

Thus, the projection angles which have this property provide data that can be completely recovered at relatively larger values of w. This means that such angles are more valuable in practical applications since they require more accessible resolution in the observations.

The distances between each adjacent projected image of the vertices of pixels define the regions along $\theta^\perp$ which, when separately sampled and averaged, determine the projection data, $P_\theta f$. A vertex of a pixel in an $L \times L$ reconstruction that has $n^2$ uniform pixels can be represented by L(s, t)/n where $0 \leq s, t \leq n$ and s and t are integers. The distance between the projected images of $L(s_1, t_1)/n$ and $L(s_2, t_2)/n$ in the direction $\theta = $ arctan p/q is given by the expression:

$$L/n \, |p(s_1 - s_2) - q(t_1 - t_2)| \, (p^2 + q^2)^{-\frac{1}{2}}.$$

For the general case, the distances may be calculated as follows: Assume for the purposes of this discussion, that the pixel 5 in FIG. 2 is an $L \times L$ square reconstruction divided into $n^2$ uniform pixels (not shown). Let the reconstruction be situated in the plane of an x, y coordinate system 7 with, as seen in FIG. 2, the lower left-hand corner located at the origin 8. Let the line, $\theta^\perp$, also be located in the same plane so that it intersects the origin. As explained, the set of projected images of the vertices of the $n^2$ pixels (not shown) that is, assumed to make up the reconstruction, $v_1, v_2, \ldots, v_k, v_{k+1}$, would lie on the line $\theta^\perp$. The distance along the line $\theta^\perp$, between each adjacent vertex projection can be defined in terms of the distance of the projected vertex, $v_j$, from the origin 8 by the expression:

$$L/n \, (ps_j - qt_j) \, (p^2 + q^2)^{-\frac{1}{2}}.$$

This point, $v_j$, ($v_j$ is the projection onto the line $\theta^\perp$ of the vertex $L/n$ ($s_j$, $t_j$)) will lie on the line $\theta^\perp$ above the x-axis (FIG. 2) if the expression is greater than zero; conversely, the point, $v_j$, will lie below the x-axis if the expression is less than zero.

Since resolution in the projection data is often a limiting empirical factor, and because the angles specified above seem to require the least restrictive resolution, these angles seem to be the most useful for practical applications.

The resolution of the reconstruction depends on the availability of a reasonable amount of resolution in the projection data when the projection angles are selected from the set stated above. Recall that the resolution of a reconstruction is defined herein as the size of the smallest square of Z(n) and is represented by L/n. A reconstruction, h, is of no value if it is not uniquely determined by its projection data. (A further and more rigorous explanation of the effect on non-uniqueness is presented in the Thesis, described above.) The term resolution of reconstruction is only meaningful when it refers to a reconstruction that is uniquely determined.

As pointed out above, in the type of reconstruction space considered here, that is, a raster or grid-like display divided into $n^2$ uniform smaller pixels, resolution of a reconstruction depends upon the number of smaller pixels used to display information. Thus, to obtain a resolution of reconstruction as fine as desired, the reconstruction space should be divided into as many smaller pixels as required. But, there is a limit on such a resolution which, if exceeded, destroys the uniqueness of the reconstruction. However, it has been found that uniqueness of the reconstruction is preserved as long as:

$$n < 1 + \max\left(\sum_{j=1}^{m} |p_j|, \sum_{j=1}^{m} |q_j|\right) \quad (4)$$

where m is the number of projection angles used.

The first 72 projection angles for any reconstruction from projection technique utilizing the principles outlined herein are listed in Table I, below. Not all these angles will be used for every particular circumstance. Rather, given a selected resolution in the reconstruction space, Z(n), only those angles, $\{\theta_1, \theta_2, \ldots, \theta_m\}$ are selected from the set, $\bar{\theta}(n)$, so that the projection data, $P_\theta f$, produced by each projection requires resolution in the projection data (as defined by expression (3), above) that is greater than w; that is, the following must be true: for $j \leq m$, $$L/n \, (p_j^2 + q_j^2)^{-\frac{1}{2}} > w. \quad (5)$$

TABLE I

| m | $P_m$ | $q_m$ | $\theta_m$ | Resolution |
|---|---|---|---|---|
| 1 | 1 | 0 | 00.0000 | 1.00000 |
| 2 | 0 | 1 | 90.0000 | 1.00000 |
| 3 | 1 | 1 | 45.0000 | 0.707 |
| 4 | 1 | −1 | −45.0000 | 0.707 |
| 5 | 2 | 1 | 26.565057 | .44721355 |
| 6 | 1 | 2 | 63.434961 | .44721355 |
| 7 | 2 | −1 | −26.565057 | .44721355 |
| 8 | 1 | −2 | −63.434961 | .44721355 |
| 9 | 3 | 1 | 18.434952 | .31622776 |
| 10 | 1 | 3 | 71.565064 | .31622776 |
| 11 | 3 | −1 | −18.434952 | .31622776 |
| 12 | 1 | −3 | −71.565064 | .31622776 |

TABLE I-continued

| m | $p_m$ | $q_m$ | $\theta_m$ | Resolution |
|---|---|---|---|---|
| 13 | 3 | 2 | 33.690073 | .27735003 |
| 14 | 2 | 3 | 56.309944 | .27735003 |
| 15 | 3 | −2 | −33.690073 | .27735003 |
| 16 | 2 | −3 | −56.309944 | .27735003 |
| 17 | 4 | 1 | 14.036247 | .24253557 |
| 18 | 1 | 4 | 75.963771 | .24253557 |
| 19 | 4 | −1 | −14.036247 | .24253557 |
| 20 | 1 | −4 | −75.963771 | .24253557 |
| 21 | 4 | 3 | 36.869904 | .19999998 |
| 22 | 3 | 4 | 53.130113 | .19999998 |
| 23 | 4 | −3 | −36.869904 | .19999998 |
| 24 | 3 | −4 | −53.130113 | .19999998 |
| 25 | 5 | 1 | 11.309935 | .19611614 |
| 26 | 1 | 5 | 78.690083 | .19611614 |
| 27 | 5 | −1 | −11.309935 | .19611614 |
| 28 | 1 | −5 | −78.690083 | .19611614 |
| 29 | 5 | 2 | 21.801413 | .1856953 |
| 30 | 2 | 5 | 68.198604 | .1856953 |
| 31 | 5 | −2 | −21.801413 | .1856953 |
| 32 | 2 | −5 | −68.198604 | .1856953 |
| 33 | 5 | 3 | 30.963762 | .17149852 |
| 34 | 3 | 5 | 59.036256 | .17149852 |
| 35 | 5 | −3 | −30.963762 | .17149852 |
| 36 | 3 | −5 | −59.036256 | .17149852 |
| 37 | 6 | 1 | 9.462324 | .16439898 |
| 38 | 1 | 6 | 80.537693 | .16439898 |
| 39 | 6 | −1 | −9.462324 | .16439898 |
| 40 | 1 | −6 | −80.537693 | .16439898 |
| 41 | 5 | 4 | 38.659815 | .15617374 |
| 42 | 4 | 5 | 51.340202 | .15617374 |
| 43 | 5 | −4 | −38.659815 | .15617374 |
| 44 | 4 | −5 | −51.340202 | .15617374 |
| 45 | 7 | 1 | 8.1301039 | .14142135 |
| 46 | 1 | 7 | 81.869913 | .14142135 |
| 47 | 7 | −1 | −8.1301039 | .14142135 |
| 48 | 1 | −7 | −81.869913 | .14142135 |
| 49 | 7 | 2 | 15.945399 | .1373605 |
| 50 | 2 | 7 | 74.054619 | .1373605 |
| 51 | 7 | −2 | −15.945399 | .137605 |
| 52 | 2 | −7 | −74.054619 | .1373605 |
| 53 | 7 | 3 | 23.198594 | .13130644 |
| 54 | 3 | 7 | 66.801422 | .13130644 |
| 55 | 7 | −3 | −23.198594 | .13130644 |
| 56 | 3 | −7 | −66.801422 | .13130644 |
| 57 | 6 | 5 | 39.805578 | .12803687 |
| 58 | 5 | 6 | 50.194438 | .12803687 |
| 59 | 6 | −5 | −39.805578 | .12803687 |
| 60 | 5 | −6 | −50.194438 | .12803687 |
| 61 | 7 | 4 | 29.744887 | .12403466 |
| 62 | 4 | 7 | 60.255131 | .12403466 |
| 63 | 7 | −4 | −29.744887 | .12403466 |
| 64 | 4 | −7 | −60.255131 | .12403466 |
| 65 | 7 | 5 | 35.537683 | .1162476 |
| 66 | 5 | 7 | 54.462333 | .1162476 |
| 67 | 7 | −5 | −35.537683 | .1162476 |
| 68 | 5 | −7 | −54.462333 | .1162476 |
| 69 | 7 | 6 | 40.601302 | .10846521 |
| 70 | 6 | 7 | 49.398714 | .10846521 |
| 71 | 7 | −6 | −40.601302 | .10846521 |
| 72 | 6 | −7 | −49.398714 | .10846521 |

The angles listed in Table I, as can be noted, are listed in a natural order determined by the use of the expression numbered (3) above, for each angle. To determine the required resolution for each angle, the term identified "Resolution" for each angle must be multiplied by L/n as shown in Eq. (5).

For example, suppose we have a square, grid-like reconstruction of side L that is divided into $n^2$ smaller squares or pixels and an available resolution, w, in the recording medium. Only those angles would be used whose required resolution is the projection data, determined by multiplying the term labled Resolution associated with each angle by L/n, meets the restriction of Eq. (5).

Therefore, the method of the present invention requires definition of the following parameters in accordance with the criteria set forth above:

1. Specifying the reconstruction space, Z(n), by selecting an appropriate n (taking care that n not exceed the limitations of Eq. 4, above);
2. Determine, empirically, the limit of the resolution in the projection data, w; and
3. Select those angles, $\theta$, from the set, $\bar{\theta}(n)$ which meet the constraints of Eq. 5, above.

Figure 4:
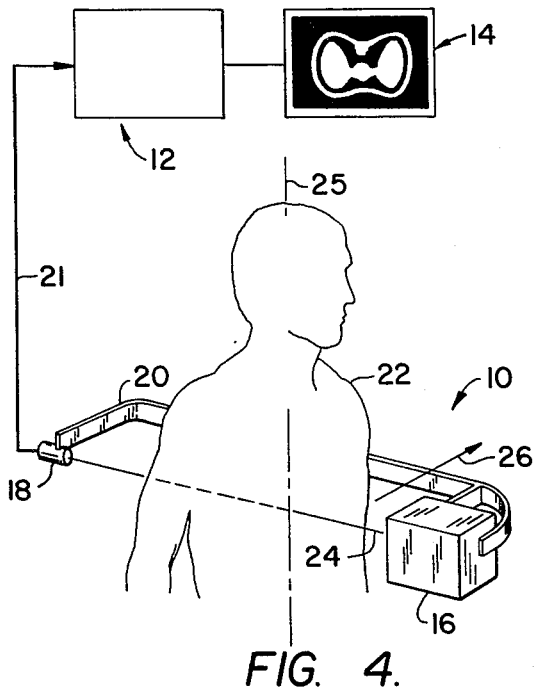
FIG. 4 is a view of an X-ray projecting system that can be used to obtain a unique reconstruction from X-ray projections according to the method of the present invention.

Referring now to FIG. 4, there is shown apparatus with which the method of the present invention may be used to obtain a uniquely determined reconstruction of a cross-section of an object, here a patient's chest, from a number of X-ray projections of that object. Such apparatus as illustrated in FIG. 4 is conventional so that only a schematic representation of that apparatus need be shown. Some minor modification of existing apparatus may be necessary so that the apparatus can be operated at the required angles. However, whatever modification that is necessary is well within the knowledge of those in the pertinent art.

Thus, FIG. 4 illustrates a system for obtaining reconstructions from projections that include an X-ray projection unit 10, computer 12, and display unit 14. X-ray unit 10 includes an X-ray generating source 16 and an X-ray detector 18. Source 16 and detector 18 are held in fixed, spaced relation to one another by yolk 20 so that a patient 22 may be interposed therebetween.

The X-ray source 16 generates parallel beams of X-rays which are directed to pass through the body of the patient 22. A collimator (not shown) made of lead is placed in front of an X-ray source (not shown) to produce the parallel beams.

The detector 18 is electrically coupled to the computer 12 by interconnect wire 21, over which is transmitted to the computer the projection data, $P_\theta f$, recorded by detector 18. The computer, in turn, is electrically coupled to the display unit 14, which is a cathode ray tube capable of displaying a rasterlike presentation.

In use, the X-ray source 16 and detector 18 move in fixed relation to each other to scan across the patient 22 in a direction perpendicular to the beam of X-rays 24 as indicated by arrow 26.

The X-rays are made to be directed so that they pass through the body 22 of the patient in parallel rays as the patient (or the X-ray apparatus 10) is rotated in steps around the single axis 25. The photographic image made at each step, that is, each projection records in effect, on a single one-dimensional line that represents structures in the patient's body lying in a plane perpendicular to the axis of rotation. The X-ray density along that line on each image isolates the information from the desired plane.

As the scan proceeds, the X-rays that pass through the patient 22 (e.g., the projection data, $P_\theta f$) are recorded by sampling the output of the detector 18 at a number of regions along each scan direction. As explained, these regions, $(v_i, v_{i+1})$, are those between the projected images of vertices of pixels in the direction $\theta$ onto the line $\theta^\perp$, discussed above. The projection data so obtained are then stored in a memory (not shown) of computer 12. The X-ray unit 10 is then rotated to the next projection angle, $\theta$, for example, and another scan made to produce projection data, $P_\theta f$, that also are recorded and stored as described above. The scan process continues until each of the selected projection angles have been used.

The projection data, $P_\theta f$, so obtained and stored in the memory (not shown) of computer 12 is then mathematically combined using any one of the reconstruction algorithms known today. For example, one such reconstruction algorithm is the ART (Algebraic Reconstruction Technique), an iterative algorithm which repeatedly modifies the estimate until the density values stop changing.

However, the reconstruction algorithm selected will require slight modification to generate the reconstruction from the projection data, $P_\theta f$. The algorithm must take into account that the projection data has varying resolution as explained above. This modification is easily accomplished by those skilled in the art and, therefore, is not described herein.

Thus, after obtaining the projection data $P_\theta f$, the computer 22, under control of the computer-implemented algorithm, transforms the projection data into the desired reconstruction which is displayed upon the display unit 14.

The method, as described, will produce reconstructions having a resolution of somewhat greater than the empirically available resolution, w, in projection data. For example, so far as is known, the present state of the art can produce an empirically available resolution in projection data no smaller than about one millimeter. A reconstruction of a cross-section of a person's head, conducted according to the above-described method, will produce a reconstruction having a resolution of about four millimeters.

This resolution can be improved, however, by a method that involves the use of purposely displaced reconstructions. Thus, for example, a uniquely determined reconstruction can be improved by a factor of two without requiring finer resolution in the data.

Figure 6A:
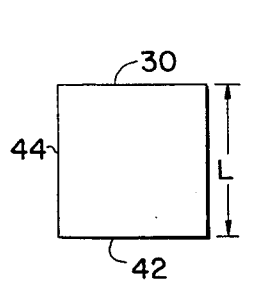
FIGS. 6A-6D schematically illustrate overlapping a number of unique reconstructions to improve resolution of the final reconstruction.

Consider, for the moment, a reconstruction obtained according to the method of the present invention and displayed on the 1 × 1 grid 30 illustrated in FIG. 6A (e.g., n = 1 = L and the reconstruction space, Z(1), is a 1 × 1 space). X-ray projections for the square reconstruction 30 would be taken. Let the term "a" express the value of the reconstruction on that square.

Figure 6B:
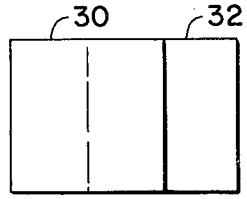
Figure 6C:
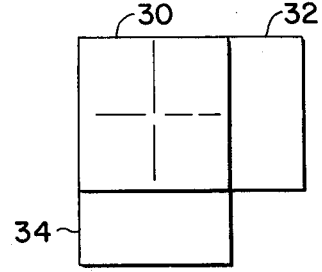
Figure 6D:
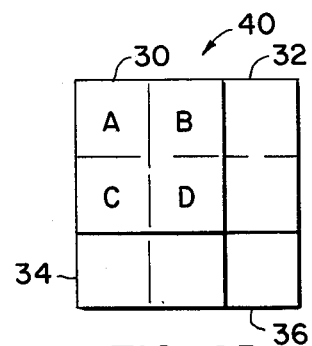

After all required projections have been completed and the resulting projection data processed by the computer 12 to form the reconstruction 30, the X-ray unit 10 is reused so that a second set of projections are taken with the resulting projection data used to form reconstruction 32 (FIG. 6B) which is displaced a distance L/n2. Let the term "b" express the value of reconstruction 32. Two more reconstructions 34 and 26 at similar displacements are made, taking on values c and d, i.e., projections are taken so that 1 × 1 (n × n) reconstructions 34 and 36 are formed (FIGS. 6C and 6D). The displacement of the third reconstruction 34 is L/n2 from the first reconstruction 30 in a direction perpendicular to the direction of the displacement of the second reconstruction 32 from the first reconstruction. Similarly, the displacement of the fourth reconstruction 36 is L/n2 from the second reconstruction 32 and L/n2 from the third reconstruction.

Completion of all projections will provide projection data that is processed to form the reconstruction 40 (FIG. 6D) composed of displaced and overlapping reconstructions 30, 32, 34 and 36.

Since we assume that each of the reconstructions 30–36 approximates the entire unknown objective function, f, we can use the information available in each relatively coarse reconstruction to obtain the new reconstruction 40 (comprising subsquares A, B, C and D) with resolution improved by a factor of 2. Thus, the four reconstructions 30–36 each on a 1 × 1 (n × n) grid are overlaid in a purposely displaced manner to obtain a new, 2 × 2 (2n × 2n) reconstruction 40. Then, of the 9 subsquares created by the boundaries of the reconstructions 30–36 only the four squares labeled A, B, C and D can be non-zero. This provides us with a system of four equations and four unknowns:

$$A + B + C + D = a$$
$$B \quad\quad + D = b$$
$$C + D = c$$
$$D = d \text{ which is clearly non-singular.}$$

The result is a uniquely determined reconstruction 40 that has a resolution two times better than the resolution obtained in the original (single) reconstruction 30.

It can easily be seen to those skilled in the art that the same reasoning can be employed to improve the resolution of a (unique) reconstruction obtained according to the method of the present invention by a factor of $\sqrt{z}$, where z is the number of displacements made and $\sqrt{z}$ is an integer. The general case would require the creation of z relatively coarse reconstructions that are displaced $L/n\sqrt{z}$ apart to improve the resolution by a factor of $\sqrt{z}$.

The displacement for each reconstruction requires a displacement in the reading of the projection data. It will be remembered that the projection data, for each projection, can be thought of as regions along the line $\theta^\perp$ defined by the projected images of the vertices of pixels onto that line. Each region is read and averaged to produce the projection data for the formation of reconstruction 30. To obtain the projection data for the displaced reconstruction 32, for example, the regions which are read are displaced, relative to regions read for reconstruction 30, a distance that is precisely $L \sin \theta/n\sqrt{z}$. If the displacement of the displaced reconstruction is in a direction perpendicular to reconstruction 32, $\sin \theta$ is replaced by $\cos \theta$.

Displacement of the regions for each successive displaced reconstruction is made relative to the regions used to define the regions of projection data for the reconstruction lineally adjacent. That is, if another displaced reconstruction were to be generated for display displaced to the right of reconstruction 32, the displacement of the regions to be read therefor is measured relative to the position of the regions along the line $\theta^\perp$ used for reconstruction 32.

In our example described above, the unique reconstruction 30 was improved by a factor of 2 by overlapping 4 unique reconstructions (30–34) displaced a distance L/n2 from one another, to achieve unique reconstruction 40 (FIGS. 6A–6D).

Thus, there has been shown a method by which uniquely determined reconstructions may be obtained of a cross-section of an object, for example, a patient's body, from a number of radiographic projections of that object. The advantages from such a method are immediately evident when it is realized that heretofore, according to available literature, only 80 percent to 90 percent accuracy has been obtained with the present state-of-the-art apparatus and methods.

A method which obtains a reconstruction that is uniquely determined is invaluable to the physician in determining the internal structures of the body by non-invasive procedures. The physician need not require such a multiplicity of different diagnostic techniques, but rather, can with more assurance rely on a reconstruction from projections technique that utilizes the method disclosed herein to long as the restrictions and limitations set forth above are observed.

While the above provides a complete disclosure of the preferred embodiment of the method of the present invention, various modifications and equivalents may be employed without departing from the true spirit and scope of the invention. For example, the data is to be read on intervals, for each projection angle, defined as being no greater than L/n times the quantity $$(p^2 + q^2)^{-\frac{1}{2}}.$$

However, if it is desired to reach the projection data on a fixed interval for all projection angles, any fixed interval may be used just as long as the interval selected is within the criteria set by expressions (3) and (5), above; that is, the fixed interval is defined by the expression $$\min[L/n \ (p_i^2 + q_i^2)^{-\frac{1}{2}}] > w.$$

Further, reference has been made to the use of X-rays for projecting an image of the object, X-rays are not the only means of making projections of structures within the body. Transmitted ultrasound, gamma rays from radioactive isotopes either inside or outside the body, fast atomic particles from accelerators, even magnetic fields — all can be made to yield their own kind of projections of the body's internal structures.

Figure 5:
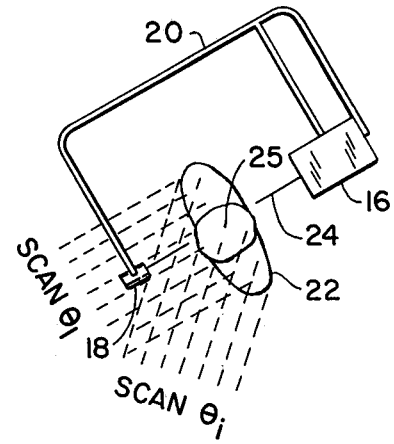
FIG. 5 is a top plan view of FIG. 4.

Finally, it should be noted that application of the method of the present invention with the apparatus described (FIGS. 4 and 5) will produce, for each projection, a projected (or photographic) image of the object in the form of a one-dimensional line; that is, for each projection, structures in the patient's body 22 lying in a plane perpendicular to the axis of rotation a (FIG. 4) would be recorded on the detecting medium, here detector 10, as a one-dimensional line. The X-ray density along that line on each image is measured to isolate the information of the objective function, f, from the desired plane which is used to reconstruct the single two-dimensional plane that appears on display unit 14. However, projection data could, in principle, be obtained from a set of ordinary projected images, made by allowing X-rays to diverge from a source, pass through the object, and then fall on a recording medium such as, for example, a sheet of photographic film. But making certain that the images are properly aligned and then transferring the data from the recording medium into a computer is presently a major undertaking. For this reason the special-purpose instruments in use today reconstruct cross-sectional planes of an object by directing parallel beams of X-rays through the object.

Therefore, the above description and illustrations should not be construed as limiting the scope of the method of the present invention, which is defined by the appended claims.

What is claimed is:

1. In a system having means for projecting a plurality of parallel X-ray images of an object onto a recording medium having a resolution of w, means for sampling the recording medium to obtain therefrom projection data representative of said images, means responsive to the sampling means for combining said projection data to generate therefrom a reconstruction representative of the object in the form of a square of side L, grid-like presentation divided into $n^2$ smaller squares, n being smaller than or equal to the quantity $$\max\left(\sum_{j=1}^{m}|p_j|, \sum_{j=1}^{m}|q_j|\right)$$

where $p_j$ and $q_j$ are relatively prime integers, m is the number of X-ray images obtained, and $0 \leq |p|, |q| \leq n$, and means responsive to the combining means for displaying the presentation, the method of obtaining the X-ray images so that the object reconstructed will be uniquely determined, the method comprising:

orienting the X-ray projecting means about an axis through the object at each one of a number of predetermined angles $\{\theta_1, \theta_2, \ldots, \theta_m\}$ and projecting an X-ray image of the object at each orientation, each of the angles $\{\theta_1, \theta_2, \ldots, \theta_m\}$ being selected from a set of angles $\theta(n)$ with elements of the form $\theta = \arctan p/q$, orientation of the X-ray projecting means at each of the angles $\{\theta_1, \theta_2, \ldots, \theta_m\}$ providing resolution in the projection data that is at least as large or larger than w and defined by L/n times the quantity $$(p^2 + q^2)^{-\frac{1}{2}}.$$

2. A method for obtaining a uniquely determined image reconstruction of an object for presentation in an L × L square, grid-like arrangement that is divided into $n^2$ smaller squares, from a series of projections of the image of the object, the method comprising the steps of:

projecting a number of images of the object onto a recording medium having a resolution of w, each of the projections being oriented with respect to a predetermined reference angle $\theta$ defined by $\theta = \arctan p/q$ where p and q are relatively prime integers and $0 \leq |p|, |q| \leq n$, each projection producing projection data having a resolution, defined by the expression $$L/n \ (p^2 + q^2)^{-\frac{1}{2}},$$

that is greater than or equal to the resolution of the recording medium;

combining the projections obtained to produce an image reconstruction of the object; and displaying the image reconstruction on a display means having n squares on a side, n being less than or equal to $$\max\left(\sum_{j=1}^{m}|p_j|, \sum_{j=1}^{m}|q_j|\right)$$

where m is the number of projected images obtained.

3. The method of claim 2, wherein the projecting step is repeated z times to obtain z projections for each angle for generating z image reconstructions of the object; and the displaying step includes displaying the z image reconstructions in an ordered spaced relation $L/(n\sqrt{z})$ units from one another to achieve an improvement of the final reconstruction by a factor of $\sqrt{z}$ where $\sqrt{z}$ is an integer and $L/(n\sqrt{z}) \geq w$.

4. A method for obtaining a uniquely determined image reconstruction of a cross-section of an object for display as an L × L picture consisting of an array of n uniform squares on a side, the method comprising the steps of:

passing a plurality of parallel, co-planar X-ray beams through the object along m lines substantially perpendicular to said beams and onto an X-ray sampling means that records the X-ray density of said beams, each one of said lines being oriented with respect to a predetermined reference an angle $\theta$ defined by $\theta = \arctan p/q$ where p and q are relatively prime integers, $0 \leq |p|, |q| \leq n$ and the minimum distance between two adjacent X-ray beams able to be discriminated by the sampling means be less than or equal to $L/n (p^2 + q^2)^{-\frac{1}{2}}$;

reading the X-ray density along each one of the lines recorded by the sampling means to obtain projection data representative of a projected image of the objects;

combining the projection data obtained from each one of the recorded lines to generate an image reconstruction approximation of the object therefrom; and displaying the image reconstruction on the display means where n is restricted to being less than or equal to $$\max \left( \sum_{j=1}^{m} |p_j|, \sum_{j=1}^{m} |q_j| \right).$$

* * * * *